(12) United States Patent
Anspach et al.

(10) Patent No.: US 6,969,368 B2
(45) Date of Patent: Nov. 29, 2005

(54) SUCTION AND DIRECTIONAL IRRIGATION APPARATUS

(75) Inventors: Thomas D. Anspach, Jupiter, FL (US); J. Thomas Roland, Jr., Bronx, NY (US); Werner Schad, Neuhausen (DE)

(73) Assignee: The Anspach Effort, Inc., Palm Beach Gardens, FL (US)

( * ) Notice: Subject to any disclaimer, the term of this patent is extended or adjusted under 35 U.S.C. 154(b) by 0 days.

(21) Appl. No.: 10/655,553

(22) Filed: Sep. 2, 2003

(65) Prior Publication Data

US 2005/0049547 A1    Mar. 3, 2005

(51) Int. Cl.[7] ............................................... A61M 1/00
(52) U.S. Cl. ........................................ 604/27; 607/30
(58) Field of Search ................. 604/533, 534, 604/27, 35, 39, 40, 43, 535, 529, 19, 173, 604/30

(56) References Cited

U.S. PATENT DOCUMENTS 3,823,720 A * 7/1974 Tribble .......................... 604/43
5,334,167 A * 8/1994 Cocanower ................. 604/523

* cited by examiner

Primary Examiner—Kevin C. Sirmons
(74) Attorney, Agent, or Firm—Norman Friedland

(57) ABSTRACT

A hand-held directional irrigation tube and a suction tube surgical instrument includes a finger or thumb operated aperture on the suction tube communicating with the lumen thereof that serves to selectively by-pass and connect the suction pump with the surgical site and the irrigation tube being removably supported in a sleeve attached to the suction tube that includes a gear-like member having circumferentially spaced valleys or slots attached to the sleeve cooperating with a projection attached to the irrigation tube so that the surgeon can slide the irrigation tube to disengage the projection and rotate it and re-insert it into another slot in the gear-like member to re-direct the spray of irrigation fluid egressing from the irrigation tube to different locations in the surgical site.

9 Claims, 2 Drawing Sheets

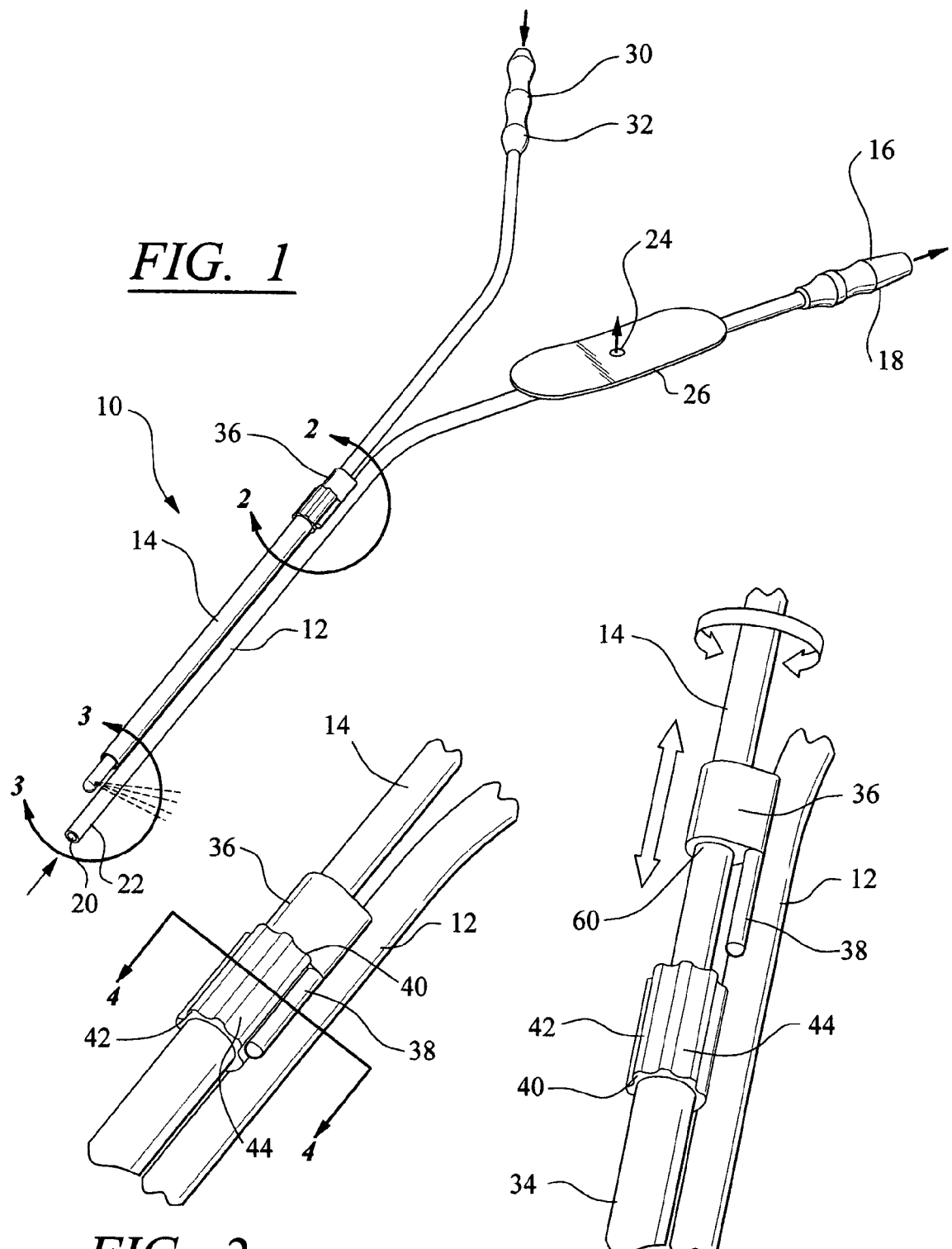

SUCTION AND DIRECTIONAL IRRIGATION APPARATUS

TECHNICAL FIELD

This invention relates to surgical devices that are utilized in surgical procedure on a patient where the surgeon requires both irrigation and suction capabilities and particularly, to a simple, hand-held, easy to use, combined suction and irrigation instrument that includes mechanism for obtaining positive directional capabilities for the irrigator portion of the instrument.

BACKGROUND OF THE INVENTION

As is well known in the medical technology when surgeons perform minimal invasive surgery as, for example, arthroscopic, laparoscopic or endoscopic surgical procedures, it is often necessary to supply irrigation fluid or to remove fluid from the surgical site. There are a sundry of such instruments that are available and described in the literature. Obviously, for achieving an effective and efficient surgical procedure with a minimal of trauma to the patient, the probe for providing irrigation fluid or for the removal of fluid from the surgical site needs to be small, simple and easy to operate.

An example of a suction/irrigation probe is described in U.S. Pat. No. 6,086,554 granted to Humphreys, Jr. et al on Jul. 11, 2000 entitled SURGICAL SUCTION/IRRIGATION PROBE ASSEMBLY WITH A ROTATABLE ADAPTOR where the adaptor is rotatable 360 degree (°) about an axis and connects to a plurality of tubes that include a supply of irrigation fluid or to a suction pump that removes liquid from the surgical site. A single tube is operatively connected to the adaptor to allow for the connection to anyone of the ports. Hence, a single outlet is configured to supply the irrigation fluid or the suction to a surgical site and a switch in the hand piece allows the surgeon to choose to supply either irrigation fluid or the vacuum.

Other types of irrigation and suction instruments are commonly used and described in the literature for performing these functions for eye surgery and stomach pumping. For example, U.S. Pat. No. 883,583 entitled STOMACH PUMP granted to Stallsmith in Mar. 31, 1908 describes a stomach pump that include induction and eduction tubes mounted side by side that is intended to fit through the esophagus. U.S. Pat. No. 6,340,355 entitled INTRAOCULAR IRRIGATION/ASPIRATION DEVICE granted to Barrett on Jan. 22, 2002 describes apparatus that includes a pair of concentric tubes with the inner tube including a lumen having a bulbous portion on the distal end with a side orifice for flowing irrigation fluid and alternately providing a lumen for the suction function. The outer tube is made from an elastomeric material so that it is flexible, while the inner tube is metallic and rigid.

Other types of irrigation and suction medical instruments are intended to be used for different medical procedures and hence, include various tips that attach to the distal end of the instrument. An example of this type is instrument is described in U.S. Pat. No. 5,792,098 that include various sizes of irrigation tips that are removably connected to a hand-held irrigation/suction hand piece.

While these instruments described in the above paragraph are capable of performing the functions described in this literature, we have found that we can provide the irrigation/suction function in a more simplified apparatus that gives the surgeon a good feel in handling the device with the capability of automatically applying the suction to the surgical site by a simple movement of a thumb or finger and that the direction of the irrigation is adjustable by a simple lifting and rotation of the irrigation tube with the assurance that the direction of the jet stream of irrigation fluid is held constant until changed by the surgeon. The invention is characterized as being uncomplicated and relatively inexpensive to manufacture, easy to operate, having a good feel for the surgeon, being reliable with the capability of applying suction or directional irrigation by a simple hand operated procedure.

SUMMARY OF THE INVENTION

The object of this invention is to provide an improved suction and directional irrigation instrument that is used in the performance of medical procedures.

A feature of this invention is the inclusion of a sleeve for supporting one of the tubes to the other tube so that the irrigation tube is adjustable for changing the direction of the jet of the irrigation fluid discharging therefrom.

Another feature of this invention is providing a by-pass in the suction lumen of the suction tube that allows the selective application of suction to the surgical site by a positioning of the finger or thumb of the surgeon.

This invention is characterized as being a hand-held irrigation/suction apparatus that is simple to make, relatively inexpensive, ease of use with a good feel for the surgeon and provides directional irrigation and the ability to apply the suction by a mere movement of the finger or thumb of the surgeon.

The foregoing and other features of the present invention will become more apparent from the following description and accompanying drawings.

BRIEF DESCRIPTION OF THE DRAWINGS

FIG. 1 is a perspective view of the suction/directional irrigation apparatus of this invention;

FIG. 2 is a fragmentary perspective enlarged view of the mechanism for changing the direction of the irrigation portion of the suction/directional irrigation apparatus taken from lines 2—2 of FIG. 1;

FIG. 2a is a view identical to the portion of the device depicted in FIG. 2 illustrating the movement of the irrigation tube during the process of changing direction;

Figure 3:
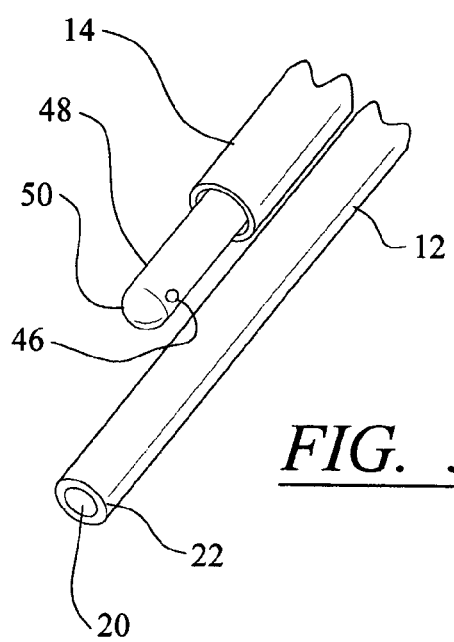
FIG. 3 is a partial view in perspective of the instrument depicted in FIG. 1 illustrating the relationship of the directional irrigation discharge orifice and the suction tube of this invention.
Figure 4:
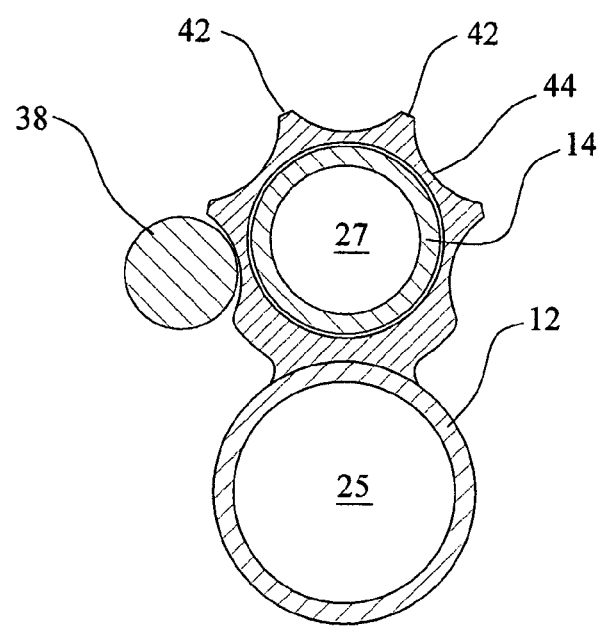
FIG. 4 is an enlarged sectional view taken along the lines 4—4 of FIG. 2.

These figures merely serve to further clarify and illustrate the present invention and are not intended to limit the scope thereof.

DETAILED DESCRIPTION OF THE INVENTION

The invention is best illustrated by referring to all of the FIGS. which show the suction and directional irrigation apparatus generally illustrated by reference numeral 10 as comprising a suction tube 12 and an irrigation tube 14 made from a suitable surgical metallic material, each having a lumen for providing the irrigation and suction functions to a surgical site. The suction tube 12 includes a fitting 16 at the proximal end 18 for attaching to a suction line or hose (not shown) and an inlet 20 at the distal end 22. The suction tube 12 includes an orifice 24 that communicates with the suction lumen 25 and a thumb or finger platen or curved dish 26 with the continuation of the orifice 24 affixed to the outer surface of suction tube 12 and located adjacent to the proximal end so as to afford easy access to the surgeon. When the suction tube is in operation, i.e. connected to a suction pump (not shown) the path of the suction or vacuum is through the hose (not shown), the fitting 16 and orifice 24 (when in the un-blocked position), the path of the suction or vacuum includes the orifice 24 and hence, by-passes the inlet 20 of the suction tube 12. In other words, when the surgeon desires not to place a vacuum in the surgical site, he leaves his finger or thumb off of orifice 24 so that the vacuum by-passes the surgical site (not shown). To connect the inlet to the suction pump via the fitting 16 and hose (not shown) the surgeon merely places a thumb or finger of his hand over the orifice 16, closing it off, so the path is not short circuited and connects the surgical site directly to the vacuum pump (not shown). Toward the proximate end the suction tube 12 and the irrigation tube are bent so as to provide space for the surgeon to hold the apparatus 10 and rest his finger or thumb on or in the vicinity of the orifice 24.

The irrigation tube 14 also includes fitting 30 at the proximate end 32 of the irrigation tube 14 which similar to the fitting 18 serves to accommodate a hose or the like (not shown) connected to the irrigation fluid source (not shown). Irrigation tube is retractable and removable and is supported in sleeve 34 which, in turn, is affixed to the outer surface of suction tube 12. The irrigation tube 14 carries a ring-like member 36 which carries a downwardly (in the direction of the distal end) projecting cylindrical rod 38. Affixed to or made integral with sleeve 34 is the gear-like ring member 40 that includes sinusoidally configured hills 42 and valleys 44 and the valleys 44 complement the rod 38 so that the rod 38 fits into these valleys as will be described in more detail hereinbelow.

The discharge aperture 46 at the distal end 48 of the irrigation tube 14 communicates with the irrigation lumen 27 and is located at the side surface thereof spaced from the end 50. The means to change the direction of the jet stream egressing from the discharge aperture 46, is by lifting the tube 14 in the direction toward the proximat end 32 to pass the end 41 of the gear-like member 40 and then, rotating the gear-like member 40 to fit into any of the other valleys 44 of the gear-like member 40.

The design of this suction and directional irrigation apparatus locates the distal end 22 of the suction tube 12 to protrude beyond the distal end 48 of the irrigation tube 14. The distance of separation of the ends is determined by the shoulder 60 of the ring-like member 36 that abuts against the end face 62 of the gear-like member 40.

In operation, the surgeon simply closes and opens the aperture 24 to turn on and off the suction from the surgical site and raises and turns the irritation tube 14 as shown in FIG. 2a to change the direction of the jet stream of the irrigation liquid discharging therefrom. Not only is this apparatus user friendly, it is easily autoclaved for being reused and simple and inexpensive to manufacture. Users of this instrument indicate that it has a good feel and facilitates that process in the overall medical procedure.

Although this invention has been shown and described with respect to detailed embodiments thereof, it will be appreciated and understood by those skilled in the art that various changes in form and detail thereof may be made without departing from the spirit and scope of the claimed invention.

It is claimed:

1. A combined suction and directional irrigation apparatus for use in a surgical procedure including an irrigation tubular member having a lumen connected to a source of irrigation fluid and a suction tubular member having a lumen connected to a suction source, a discharge port on the side surface at the distal end of said irrigation tubular member for discharging irrigation fluid into the surgical site, said irrigation tubular member being removably supported to said suction tubular member, and means attached to said irrigation tubular member and said suction tubular member for positioning said discharge port to change the direction of said discharge port for delivering irrigation fluid to a different area in the surgical site with said irrigation tubular member having a sleeve affixed to said suction tubular member disposed intermediate the ends thereof, said irrigation tubular member being slidably and removably supported by said sleeve, said means including a gear-like member affixed to said sleeve and a projection member affixed to said irrigation tubular member adapted to slide out of and into one of a plurality of slots of said gear-like member and rotated to fit into anyone of said plurality of slots, whereby said projection member is removable from any of said plurality of slots by raising and lowering said tubular member.

2. A combined suction and directional irrigation apparatus for use in a surgical procedure including an irrigation tubular member having a lumen connected to a source of irrigation fluid and a suction tubular member having a lumen connected to a suction source, an discharge port on the side surface at the distal end of said irrigation tubular member for discharging irrigation fluid into the surgical site, means operatively connected to said irrigation tubular member and said suction tubular member for changing the direction of said discharge port for delivering irrigation fluid to different areas in said surgical site, said suction tube having a finger or thumb rest member mounted thereon intermediate the ends thereof and an aperture formed in said finger or thumb rest communicating with the lumen of said suction tubular member, whereby the suction inlet of said lumen in said suction tubular member is connected or disconnected from the suction source when the finger or thumb opens and closes said aperture.

3. A combined suction and directional irrigation apparatus for use in a surgical procedure as claimed in claim 2 wherein said irrigation tubular member includes a distal end and said suction tubular member includes a distal end and said distal end of said suction tubular member projects beyond said distal end of said irrigation tubular member.

4. A combined suction and directional irrigation apparatus for use in a surgical procedure as claimed in claim 2 wherein said finger or thumb rest member is shaped in a concaved configuration to conform with the shape of the finger or thumb.

5. A surgical apparatus for providing irrigation and suction to the surgical site of a patient including a first tubular member having a lumen for directing a spray of irrigation fluid to the surgical site, a second tubular member having a lumen for directing a suction to the surgical site, a sleeve attached to said second tubular member intermediate the ends thereof for removably supporting said first tubular member thereto, a ring-like member affixed to said sleeve, an axially projecting m ember affixed to said first tubular member at a location intermediate the ends thereof for sliding into a plurality of circumferentially spaced axial slots formed in said ring-like member for selectively positioning said first tubular member in different directions, whereby the direction of the spray of irrigation fluid is variable.

6. A surgical apparatus for providing irrigation and suction to the surgical site of a patient including a first tubular member having a lumen for directing a spray of irrigation fluid to the surgical site, a second tubular member having a lumen for directing a suction to the surgical site, said second tubular member having a proximal end and fitting for attaching to asuction source and a distal end having an opening for admitting fluid and particles at the surgical site for the removal thereof, an orifice operatively connected to said lumen located intermediate the distal end and proximal end for by-passing surgical site so that the vacuum is diverted through said orifice and accessible to the surgeon for opening and closing said orifice with his finger or thumb and a platen attached to said suction tubular member having a outer surface contoured to define a finger or thumb rest, a sleeve attached to said suction tubular member for accepting said irrigation tubular member for reciprocal and rotary movement and means cooperating with said irrigation tubular member and sleeve for positioning said irrigation tubular member in different circular directions and said distal end of said suction tubular member projecting beyond the distal end of said irrigation tubular member.

7. A surgical apparatus as claimed in claim 6 wherein said means includes a gear-like member attached to and surrounding the outer surface of said sleeve and having a plurality of spaced teeth defining circumferentially spaced slots, said suction tubular member being attached to said gear-like member at one of said plurality of spaced slots, and a ring-like member having a projection affixed to said irrigation tubular member and selectively adapted to fit into one of said spaced slots, said ring-like member having a shoulder that abuts against said gear-like member to define the spacing between the distal end of said suction tubular member and the distal end of said irrigation tubular member.

8. A surgical apparatus as claimed in claim 7 including a discharge port on the side surface of said irrigation tubular member adjacent to said distal end thereof whereby the irrigation fluid is aimed at different directions in the surgical site when the surgeon raises and turns said irritation tubular member to insert said projection into any of said plurality of slots.

9. A suction and directional irrigation hand-held apparatus for irrigating and removing fluid and particles at a surgical site, said apparatus having an irrigation tube having a distal end, a proximate end and a lumen, a suction tube having a distal end, a proximate end and a lumen, a sleeve having a gear-like member surrounding the peripheral surface of said irrigation tube and being affixed to the peripheral surface of said irrigation tube at a valley between teeth of said gear-like member, said suction tube having an inlet at the distal end for admitting fluid and particles into said lumen at the surgical site, a fitting at the proximate end adapted to be connected to a vacuum source, a platen affixed intermediate the distal end and proximate end of said suction tube and located at the proximate end portion where the apparatus is held by hand and having an aperture communicating with the lumen to connect the vacuum to ambient and being adapted to be closed by the finger or thumb of the hand so as to by-pass the surgical site when opened and to connect the vacuum to the surgical site when closed, a ring-like member surrounding the periphery of said irrigation tube having an axial projection facing the distal end of said irrigation tube and complementing the valley between teeth of said gear-like member, said irrigation tube being slidably and rotatably mounted in said sleeve, said gear-like member having a shoulder at the upper end thereof, and said ring-like member having a shoulder at the lower end thereof for engagement so as to position the distal end of said irrigation tube to be upwardly spaced from the said inlet, said irrigation tube adapted to be slidably removed from a valley between teeth of said gear-like member and rotated to be inserted into another valley of said gear-like member to change the direction of the discharge port formed at the peripheral surface at the distal end of said irrigation tube and said irrigation tube having a fitting at the peripheral end thereof adapted to be connected a source of irrigation fluid whereby the surgeon holding the hand-held apparatus can selectively apply suction to the surgical suction and can mechanically change the direction of the flow of irrigation fluid at the surgical site.

* * * * *